United States Patent
Zou et al.

(10) Patent No.: US 10,435,753 B2
(45) Date of Patent: Oct. 8, 2019

(54) METHODS FOR DETECTING COLORECTAL CANCER USING A DNA MARKER OF EXFOLIATED EPITHELIA AND A FECAL BLOOD MARKER

(71) Applicant: Mayo Foundation for Medical Education and Research, Rochester, MN (US)

(72) Inventors: Hongzhi Zou, Middleton, WI (US); David Ahlquist, Rochester, MN (US); Jonathan J. Harrington, Madison, WI (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 750 days.

(21) Appl. No.: 14/954,496

(22) Filed: Nov. 30, 2015

(65) Prior Publication Data

US 2016/0083803 A1    Mar. 24, 2016

Related U.S. Application Data

(63) Continuation of application No. 13/072,047, filed on Mar. 25, 2011, now abandoned.

(60) Provisional application No. 61/318,077, filed on Mar. 26, 2010.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57419* (2013.01); *C12Q 2600/154* (2013.01); *C12Q 2600/156* (2013.01); *G01N 2333/805* (2013.01); *G01N 2800/50* (2013.01); *G01N 2800/7028* (2013.01)

(58) Field of Classification Search
None
See application file for complete search history.

(56) References Cited

U.S. PATENT DOCUMENTS

| | | |
|---|---|---|
| 5,352,775 A | 10/1994 | Albertsen |
| 5,362,623 A | 11/1994 | Vogelstein |
| 5,527,676 A | 6/1996 | Vogelstein |
| 5,541,308 A | 7/1996 | Hogan |
| 5,648,212 A | 7/1997 | Albertsen |
| 5,670,325 A | 9/1997 | Lapidus |
| 5,691,454 A | 11/1997 | Albertsen |
| 5,741,650 A | 4/1998 | Lapidus |
| 5,783,666 A | 7/1998 | Albertsen |
| 5,786,146 A | 7/1998 | Herman |
| 5,928,870 A | 7/1999 | Lapidus |
| 5,952,178 A | 9/1999 | Lapidus |
| 5,955,263 A | 9/1999 | Vogelstein |
| 6,020,137 A | 2/2000 | Lapidus |
| RE36,713 E | 5/2000 | Vogelstein |
| 6,090,566 A | 7/2000 | Vogelstein |
| 6,114,124 A | 9/2000 | Albertsen |
| 6,245,515 B1 | 6/2001 | Vogelstein |
| 6,413,727 B1 | 7/2002 | Albertsen |
| 6,677,312 B1 | 1/2004 | Vogelstein |
| 6,800,617 B1 | 10/2004 | Vogelstein |
| RE38,916 E | 12/2005 | Vogelstein |
| 7,037,650 B2 | 5/2006 | Gonzalgo et al. |
| 7,087,583 B2 | 8/2006 | Vogelstein |
| 7,267,955 B2 | 9/2007 | Vogelstein |
| 7,432,050 B2 | 10/2008 | Markowitz |
| 7,485,402 B2 | 2/2009 | Arai |
| 7,485,418 B2 | 2/2009 | Goggins |
| 8,361,720 B2 | 1/2013 | Oldham-Haltom |
| 8,808,990 B2 | 8/2014 | Lidgard et al. |
| 8,969,046 B2 | 3/2015 | Van Engeland et al. |
| 8,980,107 B2 | 3/2015 | Domanico et al. |
| 8,993,341 B2 | 3/2015 | Bruinsma et al. |
| 8,999,176 B2 | 4/2015 | Domanico et al. |
| 9,000,146 B2 | 4/2015 | Bruinsma et al. |
| 9,506,116 B2 | 11/2016 | Ahlquist et al. |
| 2003/0224040 A1 | 12/2003 | Baylin et al. |
| 2004/0234960 A1 | 11/2004 | Hogan |

(Continued)

FOREIGN PATENT DOCUMENTS

| | | |
|---|---|---|
| EP | 2391729 | 12/2011 |
| WO | WO 00/26401 | 5/2000 |

(Continued)

OTHER PUBLICATIONS

Haug, Ulrike, and Hermann Brenner. "New stool tests for colorectal cancer screening: a systematic review focusing on performance characteristics and practicalness." International journal of cancer 117.2 (2005): 169-176.*
Tan et al. "Variable promoter region CpG island methylation of the putative tumor suppressor gene Connexin 26 in breast cancer" Carcinogenesis. 2002 23(2): 231-236.
Jin et al. "A multicenter, Double-blinded Validation study of methylation biomarkers for progression prediction in Barrett's Esophagus" Cancer Research, May 15, 2009, vol. 69, pp. 4112-4115.
Kaz et al. "DNA methylation profiling in Barrett's esophagus and esophageal adenocarcinoma reveals unique methylation signatures and molecular subclasses" Epigenetics, Dec. 1, 2011, vol. 6, pp. 1403-1412.

(Continued)

*Primary Examiner* — G Steven Vanni
(74) *Attorney, Agent, or Firm* — Casimir Jones, SC; Robert A. Goetz

(57) ABSTRACT

The present invention provides methods and materials related to the detection of colorectal neoplasm-specific markers in or associated with a subject's stool sample. In particular, the present invention provides methods and materials for identifying mammals having a colorectal neoplasm by detecting the presence of exfoliated epithelial markers (e.g., human DNA, tumor assoicated gene alterations, tumor associated proteins) and blood markers (e.g., homoglobin, serum proteins) in a stool sample obtained from the mammal.

5 Claims, 3 Drawing Sheets

Specification includes a Sequence Listing.

(56) References Cited

U.S. PATENT DOCUMENTS

| | | |
|---|---|---|
| 2006/0253259 A1 | 11/2006 | Fernandez |
| 2007/0054295 A1 | 3/2007 | Spivack |
| 2008/0081333 A1 | 4/2008 | Mori et al. |
| 2008/0213870 A1 | 9/2008 | Cao et al. |
| 2009/0208505 A1 | 8/2009 | Samuels |
| 2010/0167940 A1 | 7/2010 | Feinberg |
| 2010/0317000 A1 | 12/2010 | Zhu |
| 2011/0136687 A1 | 6/2011 | Olek et al. |
| 2011/0318738 A1 | 12/2011 | Jones et al. |
| 2012/0034605 A1 | 2/2012 | Hinoda et al. |
| 2012/0122088 A1 | 5/2012 | Zou |
| 2012/0122106 A1 | 5/2012 | Zou |
| 2012/0164110 A1 | 6/2012 | Feinberg et al. |
| 2012/0164238 A1 | 6/2012 | Joost |
| 2013/0012410 A1 | 1/2013 | Zou et al. |
| 2013/0022974 A1 | 1/2013 | Chinnaiyan |
| 2013/0065228 A1 | 3/2013 | Hinoue et al. |
| 2013/0244235 A1 | 9/2013 | Ahlquist et al. |
| 2013/0288247 A1 | 10/2013 | Mori et al. |
| 2014/0057262 A1 | 2/2014 | Ahlquist et al. |
| 2014/0137274 A1 | 5/2014 | Ishikawa |
| 2014/0193813 A1 | 7/2014 | Bruinsma et al. |
| 2014/0194607 A1 | 7/2014 | Bruinsma et al. |
| 2014/0194608 A1 | 7/2014 | Bruinsma et al. |
| 2014/0274748 A1 | 9/2014 | Ahlquist et al. |
| 2015/0126374 A1 | 5/2015 | Califano |
| 2015/0240318 A1 | 8/2015 | Van Engeland et al. |
| 2016/0194723 A1 | 7/2016 | Louwagie |

FOREIGN PATENT DOCUMENTS

| | | |
|---|---|---|
| WO | WO 2007/116417 | 10/2007 |
| WO | 2008/084219 | 7/2008 |
| WO | 2010/089538 | 8/2010 |
| WO | WO 2010/086389 | 8/2010 |
| WO | WO 2011/119934 | 9/2011 |
| WO | 2011/126768 | 10/2011 |
| WO | 2012/155072 | 11/2012 |
| WO | WO 2012/175562 | 12/2012 |

OTHER PUBLICATIONS

Zhai et al. "Genome-wide DNA Methylation Profiling of Cell-Free Serum DNA in Esophageal Adenocarcinoma and Barrett Esophagus" Neoplasia, Jan. 11, 2012, vol. 14, No. 1, pp. 29-33.

International Search Report, International Application No. PCT/US2016/023782, dated Sep. 1, 2016.

Haag S, et al., "Regression of Barrett's esophagus: the role of acid suppression, surgery, and ablative methods." Gastrointest Endosc. Aug. 1999;50(2):229-40.

Supplemental Search Report, EP Patent Application No. 157723263, dated Oct. 6, 2017.

Ahlquist D et al. (2010) "Next Generation Stool DNA Testing for Detection of Colorectal Neoplasia—Early Marker Evaluation", presented at *Colorectal Cancer: Biology to Therapy*, American Association for Cancer Research.

Ahlquist D.A. et al., "Novel use of hypermethylated DNA markers in stool for detection of colorectal cancer: a feasibility study." Gastroenterology, 2002;122(Suppl):A40.

Ahlquist D.A., et al., "Colorectal cancer screening by detection of altered human DNA in stool: feasibility of a multitarget assay panel." Gastroenterology, 2000, 119(5):1219-27.

Ahlquist et al., "Next-generation stool DNA test accurately detects colorectal cancer and large adenomas." Gastroenterology (2012), 142, pp. 248-256.

Anderson et al. Am. J. of Gastroenterology, Abstracts S1033, Oct. 2015, 1 page.

Asai et al. "IKZF1 deletion is associated with a poor outcome in pediatric B-cell precursor acute lymphoblastic leukemia in Japan." Cancer Med. 2013; 2:412-9.

Aust DE, "Mutations of the BRAF gene in ulcerative colitis-related colorectal carcinoma." Int. J. Cancer (2005), 115, pp. 673-677.

Azuara et al. "Novel Methylation Panel for the Early Detection of Colorectal Tumors in Stool DNA." Clinical Colorectal Cancer, vol. 9, No. 3, pp. 168-176, Jul. 2010.

Baxter, Eva "Investigating the association between BRAFv600E and methylation in sporadic colon cancer" PhD The University of Edinburgh, 2011, 58 pages.

Belinsky S.A., et al., "Promoter Hypermethylation of Multiple Genes in Sputum Precedes Lung Cancer Incidence in a High-Risk Cohort." Cancer Res, 2006; 66:3338-44.

Bell et al., "c-Ki-ras gene mutations in dysplasia and carcinomas complicating ulcerative colitis." Br J Cancer (1991), 64, pp. 174-178.

Biankin et al. (2003) "Molecular pathogenesis of precursor lesions of pancreatic ductal adenocarcinoma" Pathology 35:14-24.

Brune, et al. (2008). "Genetic and epigenetic alterations of familial pancreatic cancers." Cancer Epidemiol Biomarkers Prev. 17 (12): 3536-3542.

Buck et al. "Design Strategies and Performance of Custom DNA Sequencing Primers" Biotechniques, 1999, 27(3): 528-536.

Cairns et al., "Guidelines for colorectal cancer screening and surveillance in moderate and high risk groups." Gut (2010); 59, pp. 666-689.

Cameron et al (1995) "Adenocarcinoma of the esophagogastric junction and Barrett's esophagus" Gastroenterology 109: 1541-1546.

Cameron et al. Blood, vol. 94, No. 7, pp. 2445-2451, Oct. 1999.

Camoes et al. "Potential downstream target genes of aberrant ETS transcription factors are differentially affected in Ewing's sarcoma and prostate carcinoma." PLoS One. 2012;7:e49819.

Campbell et al. "Aberrant expression of the neuronal transcription factor FOXP2 in neoplastic plasma cells." British journal of haematology. 2010; 149:221-30.

Chen "Expression and promoter methylation analysis of ATP-binding cassette genes in pancreatic cancer" Oncology Reports, 2012, 27:265-269.

Chen W.D., et al., "Detection in Fecal DNA of Colon Cancer-Specific Methylation of the Nonexpressed Vimentin Gene." J Natl Cancer Inst 2005;97:1124-32.

Eads, et al. (1999). "CpG island hypermethylation in human colorectal tumors is not associated with DNA methyltransferase overexpression." Cancer Res. 59: 2302-2306.

Ebert M.P., et al., "Aristaless-like homeobox-4 gene methylation is a potential marker for colorectal adenocarcinomas." Gastroenterology 2006;131:1418-30.

Edge, S.; Fritz, A.G.; Greene, F.L.; Trotti, A. (Eds.), AJCC Cancer Staging Manual 7th ed: Springer, New York; 2010; Book—only table of contents provided.

Esteller et al. "Inactivation of Glutathione S-Transferase P1 Gene by Promoter Hypermethylation in Human Neoplasia" Cancer Resarch, vol. 58, pp. 4515-4518, Oct. 1998.

Feng "Conservation and divergence of methylation patterning in plants and animals" PNAS 2010 vol. 107, No. 19, pp. 8689-8694.

Garrity-Park et al. "Methylation status of genes in non-neoplastic mucosa from patients with ulcerative colitis-associated colorectal cancer." Am J Gastroenterol (2010), 105, pp. 1610-1619.

Glockner, et al. (2009). "Methylation of TFPI2 in stool DNA: a potential novel biomarker for the detection of colorectal cancer." Cancer Res. 69: 4691-4699.

Goggins, M. "Molecular markers of early pancreatic cancer." J Clin Oncol 2005; 23: 4524.

Gonzalgo, et al. (1997) "Identification and characterization of differentially methylated regions of genomic DNA by methylation-sensitive arbitrarily primed PCR." Cancer Res. 57: 594-599.

Gonzalgo, et al. (1997). "Rapid quantitation of methylation differences at specific sites using methylation-sensitive single nucleotide primer extension (Ms-SNuPE)." Nucleic Acids Res. 25 (12): 2529-2531.

Grady W.M., et al., "Detection of Aberrantly Methylated hMLH1 Promoter DNA in the Serum of Patients with Microsatellite Unstable Colon Cancer 1." Cancer Res, 2001;61:900-2.

(56) References Cited

OTHER PUBLICATIONS

Grutzmann et al., "Sensitive Detection of Colorectal Cancer in Peripheral Blood by Septin 9 DNA Methylation Assay." PLoS ONE (2008), 3:e3759.
Gu et al. "Genome-scale DNA methylation mapping of clinical samples at single-nucleotide resolution." Nat Methods. 2010; 7:133-6.
Gu, et al. (2011). "Preparation of reduced representation bisulfite sequencing libraries for genome-scale DNA methylation profiling." Nature Protocols. 6 (4): 468-481.
Gurung et al. "Menin epigenetically represses Hedgehog signaling in MEN1 tumor syndrome." Cancer research. 2013;73:2650-8.
Herman, et al. (1996). "Methylation-specific PCR: A novel PCR assay for methylation status of CpG islands." Proc. Natl. Acad. Sci. USA. 93: 9821-9826.
Hibi et al. (2010) "Methylation of the TFPI2 gene is frequently detected in advanced gastric carcinoma" Anticancer Res 30: 4131-3.
Hibi, et al. (2010). "Methylation of TFPI2 gene is frequently detected in advanced well-differentiated colorectal cancer." Anticancer Res. 30: 1205-1207.
Hirota et al., "pS2 expression as a possible diagnostic marker of colorectal carcinoma in ulcerative colitis." Oncol Rep (2000), 7, pp. 233-239.
Holzmann et al., "Comparative analysis of histology, DNA content, p53 and Ki-ras mutations in colectomy specimens with long-standing ulcerative colitis." Int J Cancer (1998) 76, pp. 1-6.
Hong, et al. (2008). "Multiple genes are hypermethylated in intraductal papillary mucinous neoplasms of the pancreas." Mod Pathol. 21 912): 1499-1507.
Hoque M.O., et al., "Quantitative methylation-specific polymerase chain reaction gene patterns in urine sediment distinguish prostate cancer patients from control subjects." J Clin Oncol, 2005;23:6569-75.
Howe, et al., "Annual report to the nation on the status of cancer, 1975-2003, featuring cancer among U.S. Hispanic/Latino populations." Cancer (2006) 107, pp. 1711-1742.
Imperiale et al., "Fecal DNA versus fecal occult blood for colorectal-cancer screening in an average-risk population." N Engl J Med (2004), 351, pp. 2704-2714.
International Search Report and Written Opinion, Int'l Patent Application No. PCT/US2015/022749, dated Aug. 19, 2015, 12 pages.
International Search Report and Written Opinion, Int'l Patent Application No. PCT/US2015/022751, dated Aug. 26, 2015, 25 pages.
International Search Report dated Jun. 10, 2013 from related International Patent Application No. PCT/US2013/027227.
Issa et al., "Accelerated Age-related CpG Island Methylation in Ulcerative Colitis." Cancer Res (2001), 61, pp. 3573-3577.
Itzkowitz et al. "Diagnosis and management of dysplasia in patients with inflammatory bowel diseases." Gastroenterology (2004) 126, pp. 1634-1648.
Itzkowitz S.H., et al., "Improved fecal DNA test for colorectal cancer screening." Clin Gastroenterol Hepatol 2007;5:111-7.
Jacobs et al. "Dysregulated methylation at imprinted genes in prostate tumor tissue detected by methylation microarray." BMC Urol. 2013;13:37.
Jess et al., "Risk of intestinal cancer in inflammatory bowel disease: a population-based study from olmsted county, Minnesota." Gastroenterology (2006) 130, pp. 1039-1046.
Jiao et al. "Somatic mutations in the Notch, NF-KB, PIK3CA, and Hedgehog pathways in human breast cancers." Genes, chromosomes & cancer. 2012; 51:480-9.
Kaiser. (2008). "Cancer genetics. A detailed genetic portrait of the deadliest human cancers." Science. 321: 1280-1281.
Kann L., et al., "Improved marker combination for detection of de novo genetic variation and aberrant DNA in colorectal neoplasia." Clin Chem 2006;52:2299-302.
Kawai, et al. (1994). "Comparison of DNA methylation patterns among mouse cell lines by restriction landmark genomic screening." Mol. Cell Biol. 14 (11): 7421-7427.

Kisiel et al. "New DNA Methylation Markers for Pancreatic Cancer: Discovery, Tissue Validation, and Pilot Testing in Pancreatic Juice" Clinical Cancer Research, vol. 21, No. 19, May 28, 2015, pp. 4473-4481.
Kisiel et al. "Stool DNA testing for the detection of pancreatic cancer: assessment of methylation marker candidates." Cancer. 2012; 118:2623-31.
Kisiel et al. (AGA Abstracts, VS-68, vol. 138, No. 5, May 2010).
Kisiel, et al. (2011). "Stool DNA screening for colorectal cancer: opportunities to improve value with next generation tests." J Clin Gastroenterol. 45 (4): 301-8.
Kober et al. "Methyl-CpG binding column-based identification of nine genes hypermethylated in colorectal cancer." Molecular carcinogenesis. 2011; 50:846-56.
Kraus, et al., "Inflammation and colorectal cancer," Current Opinion in Pharmacology, vol. 9, No. 4, pp. 405-410 (2009).
Kuppuswamy et al. "Single nucleotide primer extension to detect genetic diseases: Experimental application to hemophilia B (factor IX) and cystic fibrosis genes" (1991) Proc. Natl. Acad. Sci. USA 88: 1143-1147.
Laird. (2010). "Principles and challenges of genome-wide DNA methylation analysis." Nat Rev Genet. 11: 191-203.
Lashner Ba, "Evaluation of the Usefulness of Testing for p53 Mutations in Colorectal Cancer Surveillance for Ulcerative Colitis" Am J Gastroenterol (1999), 94, pp. 456-462.
Lee et al. "Pituitary homeobox 2 (PITX2) protects renal cancer cell lines against doxorubicin toxicity by transcriptional activation of the multidrug transporter ABCB1." International journal of cancer Journal international du cancer. 2013; 133:556-67.
Leung W.K., et al., "Detection of epigenetic changes in fecal DNA as a molecular screening test for colorectal cancer: A feasibility study." Clin Chem 2004; 50(11):2179-82.
Levin B, "Screening and Surveillance for Early Detection of Colorectal Cancer . . . " Gastroenterology (2008); 134, pp. 1570-1595.
Li et al. "Association between Galphai2 and ELMO1/Dock180 connects chemokine signalling with Rac activation and metastasis." Nat Commun. 2013; 4:1706.
Lim, et al. (2010). "Cervical dysplasia: assessing methylation status (Methylight) of CCNA1, DAPK1, HS3ST2, PAX1 and TFPI2 (to improve diagnostic accuracy." Gynecol Oncol. 119: 225-231.
Lin, et al., Identification of disease-associated DNA methylation in intestinal tissues from patients with inflammatory bowel disease, Clinical Genetics, vol. 80, No. 1, pp. 59-67 (2011).
Liu et al. "Medulloblastoma expresses CD1d and can be targeted for immunotherapy with NKT cells." Clin Immunol. 2013;149:55-64.
Lokk et al. "Methylation Markers of Early-Stage Non-Small Cell Lung Cancer" PLOS One, vol. 7, No. 6, e398013, Jun. 2012.
Ma, et al. (2011). "MicroRNA-616 induces androgen-independent growth of prostate cancer cells by suppressing expression of tissue factor pathway inhibitor TFPI-2." Cancer Res. 71: 583-592.
Maeda, et al., "DNA hypermethylation in colorectal neoplasms and inflammatory bowel disease: a mini review," Inflammapharmacology, vol. 14, No. 5-6, pp. 204-206 (2006).
Matsubayashi, et al. (2006). "DNA methylation alterations in the pancreatic juice of patients with suspected pancreatic disease." Cancer Res. 66: 1208-1217.
Meissner et al. (2008). "Genome-scale DNA methylation maps of pluripotent and differentiated cells." Nature. 454: 766-70.
Melotte et al., "N-Myc Downstream-Regulated Gene 4 (NDRG4): A Candidate Tumor Suppressor Gene and Potential Biomarker for Colorectal Cancer" (JNCL, vol. 101, No. 13, pp. 916-927, Jul. 2009).
Muller H.M., et al., "Methylation changes in faecal DNA: a marker for colorectal cancer screening?" The Lancet 2004;363:1283-5.
Naumov "Genome-scale analysis of DNA methylation in colorectal cancer using Infinium HumanMethylation450 BeadChips" Epigenetics, 2013, vol. 8, issue 9, pp. 921-934.
Obusez et al. "Adenocarcinoma in the ileal pouch: early detection and potential role of fecal DNA methylated markers in surveillance" (Int. J. Colorectal Dis. vol. 26, pp. 951-953, 2011).

(56) References Cited

OTHER PUBLICATIONS

Obusez et al. "Fecal methylated markers for the detection of adenocarcinoma in ileal pouches of patients with underlying ulcerative colitis" (Inflammatory Bowel Diseases: vol. 14, Issue pS42, Dec. 2008, P-0106).
Odze RD, "Genetic Alterations in Chronic Ulcerative Colitis-Associated Adenoma-Like DALMs Are Similar to Non-Colitic Sporadic Adenomas" Am J Surg Pathol (2000), 24, pp. 1209-1216.
Olaru, et al., "Unique patterns of CpG island methylation in inflammatory bowel disease-associated colorectal cancers," Inflammatory Bowel Diseases, vol. 18, No. 4, pp. 641-648 (Epub Aug. 9, 2011).
Olson, J et al. "DNA Stabilization Is Critical for Maximizing Performance of Fecal DNA-Based Colorectal Cancer Tests" Diagn Mol Pathol (2005) 14, pp. 183-191.
Omura, et al. (2008). "Genome-wide profiling of methylated promoters in pancreatic adenocarcinoma." Cancer Biol Ther. 7 (7): 1146-1156.
Omura, et al. (2009). "Epigenetics and epigenetic alterations in pancreatic cancer." Int. J. Clin Exp Pathol. 2: 310-326.
Osborn NK, and Ahlquist DA, "Stool screening for colorectal cancer: molecular approaches." Gastroenterology 2005;128:192-206.
Osborn, et al., "Aberrant methylation of the eyes absent 4 gene in ulcerative colitis-associated dysplasia," Clinical Gastroenterology and Hepatology, vol. 4, No. 2, pp. 212-218 (2006).
Oster, B. et al., "Identification and validation of highly frequent CpG island hypermethylation in colorectal adenomas and carcinomas." Int J Cancer. 2011;129(12):2855-66.
Pao et al. "The endothelin receptor B (EDNRB) promoter displays heterogeneous, site specific methylation patterns in normal and tumor cells" Human Molecular Genetics, 2001, vol. 10, No. 9, pp. 903-910.
Person et al. "Chronic cadmium exposure in vitro induces cancer cell characteristics in human lung cells." Toxicol Appl Pharmacol. 2013; 273(2):281-8.
Petko Z., et al., "Aberrantly Methylated CDKN2A, MGMT, and MLH1 in Colon Polyps and in Fecal DNA from Patients with Colorectal Polyps." Clin Cancer Res 2005;11:1203-9.
Raimondo et al. "Methylated DNA Markers in Pancreatic Juice Discriminate Pancreatic Cancer From Chronic Pancreatitis and Normal Controls" Gastroenterology 2013; 144:S-90.
Rex et al. "American College of Gastroenterology guidelines for colorectal cancer screening 2008." Am J Gastroenterol (2009); 104, pp. 739-750.
Ruppenthal et al. "TWIST1 Promoter Methylation in Primary Colorectal Carcinoma" Pathol. Oncol. Res., 2011, 17:867-872.
Sadri and Hornsby "Rapid Analysis of DNA Methylation Using New Restriction Enzyme Sites Created by Bisulfite Modification." (1996) Nucl. Acids Res. 24: 5058-5059.
Sato et al., "Aberrant methylation of the HPP1 gene in ulcerative colitis-associated colorectal carcinoma." Cancer Res (2002), 62, pp. 6820-6822.
Sato, et al. (2003). "Discovery of novel targets of aberrant methylation in pancreatic carcinoma using high-throughput microarrays." Cancer Res. 63: 3735-3742.
Sato, et al. (2008). "CpG island methylation profile of pancreatic intraepithelial neoplasia." Mod Pathol. 21 93): 238-244.
Schulmann, et al., Molecular phenotype of inflammatory bowel disease-associated neoplasms with microsatellite instability, Gastroenterology, vol. 129, No. 1, pp. 74-85 (2005).
Sen-Yo et al. "TWIST1 hypermethylation is observed in pancreatic cancer" Biomedical Reports; 1:33-33, 2013.
Seshagiri et al. "Recurrent R-spondin fusions in colon cancer." Nature. 2012; 488:660-4.
Shin et al. "Bile-based detection of extrahepatic cholangiocarcinoma with quantitative DNA methylation markers and its high sensitivity." The Journal of molecular diagnostics : JMD. 2012;14:256-63.
Singer-Sam et al. "A quantitative HpaII-PCR assay to measure methylation of DNA from a small number of cells" (1990) Nucl. Acids Res. 18(3): 687.
Singer-Sam et al. "A sensitive, quantitative assay for measurement of allele-specific transcripts differing by a single nucleotide." (1992) PCR Methods Appl. 1: 160-163.
Stumm et al. "Strong expression of the neuronal transcription factor FOXP2 is linked to an increased risk of early PSA recurrence in ERG fusion-negative cancers." Journal of clinical pathology. 2013;66:563-8.
Surdez et al. "Targeting the EWSR1-FLI1 oncogene-induced protein kinase PKC-beta abolishes ewing sarcoma growth." Cancer research. 2012;72:4494-503.
Szabo and Mann "Allele-specific expression and total expression levels of imprinted genes during early mouse development: implications for imprinting mechanisms." (1995) Genes Dev. 9(24): 3097-3108.
Tang, et al. (2010). "Prognostic significance of tissue factor pathway inhibitor 2 in pancreatic carcinoma and its effect on tumor invasion and metastatis." Med Oncol. 27: 867-875.
Taylor et al. "Expression of p53 in colorectal cancer and dysplasia complicating ulcerative colitis." Br J Surg (1993), 80, pp. 442-444.
Tonack, et al. (2009). "Pancreatic cancer: proteomic approaches to a challenging disease." Pancreatology. 9: 567-576.
Toyota, et al. (1999). "Identification of differentially methylated sequences in colorectal cancer by methylated CpG island amplification." Cancer Res. 59: 2307-2312.
Tsunoda, et al. (2009). "Methylation of CLDN6, FBN2, RBP1, RBP4, TFPI2 and TMEFF2 in esophageal squamous cell carcinoma." Oncol Rep. 21: 1067-1073.
Vincent et al. "Genome-wide analysis of promoter methylation associated with gene expression profile in pancreatic adenocarcinoma." Clinical cancer research: an official journal of the American Association for Cancer Research. 2011; 17:4341-54.
Watanabe, T., "RUNX3 copy number predicts the development of UC-associated colorectal cancer" International Journal of Oncology (2011), 38, pp. 201-207.
Wheeler et al. "Hypermethylation of the promoter region of the E-cadherin gene (CDH1) in sporadic and ulcerative colitis associated colorectal cancer." Gut (2001), 48, pp. 367-371.
Wu, "Aberrant Gene Methylation in the Neoplastic Progression of Barrett's Esophagus: Identification of Candidate Diagnostic Markers" Gastroenterology (2011) 14: S-222.
Xiong, et al. (1997). Nucleic Acids Res. 25 (12): 2532-2534.
Yachida, et al. (2010). "Distant metastasis occurs late during the genetic evolution of pancreatic cancer." Nature. 467: 1114-1117.
Yamaguchi, et al. (2005). "Pancreatic juice cytology in intraductal papillary mucinous neoplasm of the pancreas." Pancreatology. 5: 416-421.
Yang N. et al. "Methylation markers for CCNA1 and C13ORF18 are strongly associated with high-grade cervical intraepithelial neoplasia and cervical cancer in cervical scrapings." Cancer epidemiology, biomarkers & prevention : a publication of the American Association for Cancer Research, cosponsored by the American Society of Preventive Oncology. 2009;18:3000-7.
Zhang et al. (2009). "DNA methylation analysis of chromosome 21 gene promoters at single base pair and single allele resolution." PLoS Genet. 5 (3): e1000438.
Zhao et al. "Genome-wide identification of Epstein-Barr virus-driven promoter methylation profiles of human genes in gastric cancer cells." Cancer. 2013;119:304-12.
Zou H., et al., "A Sensitive Method to Quantify Human Long DNA in Stool: Relevance to Colorectal Cancer Screening." Cancer Epidemiol Biomarkers Prev 2006;15:1115-9.
Zou H.Z., et al., "Detection of aberrant p16 methylation in the serum of colorectal cancer patients." Clin Cancer Res 2002;8(1):188-91.
Zou, et al. (2007). "Highly methylated genes in colorectal neoplasia: implications for screening." Cancer Epidemial Biomarkers Prev. 16: 2686-2696.
Zou, et al. (2009). "T2036 Pan-Detection of Gastrointestinal Neoplasms by Stool DNA Testing Establishment of Feasibility." *Gastroenterology*. 136: A-625.

(56) References Cited

OTHER PUBLICATIONS

Summons to attend oral proceedings, European patent application No. 11760295.3, dated Mar. 4, 2016.
Imperiale et al. "Multitarget Stool DNA Testing for Colorectal-Cancer Screening" New England Journal of Medicine, vol. 370, No. 14, Apr. 3, 2014, pp. 1287-1297.
Park, et al. (2002), "Expressiono f melanoma antigen-encoding genes (MAGE) by common primers for MAGE-A1 to -A6 in colorectal carcinomas among Koreans," J. Korean Med. Sci 17: 497-501.
International Search Report and Written Opinion dated Dec. 28, 2011 from International Patent Application No. PCT/US2011/029959, international filing date Mar. 25, 2011.
Kim, H., et al., "Noninvasive molecular biomarkers for the detection of colorectal cancer," BMB Reports, 2008, vol. 41, No. 10, pp. 685-692.
Ahlquist et al., 1984, "HemoQuant, a new quantitative assay for fecal hemoglobin. Comparison with Hemoccult." Ann Intern Med, 101: 297-302.
Ahlquist et al., 1985, "Fecal blood levels in health and disease. A study using HemoQuant." N Engl J Med, 312: 1422-8.
Ahlquist et al., 1989, "Patterns of occult bleeding in asymptomatic colorectal cancer." Cancer, 63: 1826-30.
Ahlquist et al., 1993, "Accuracy of fecal occult blood screening for colorectal neoplasia. A prospective study using Hemoccult and HemoQuant tests." JAMA, 269: 1262-7.
Ahlquist et al., 2000, "Colorectal cancer screening by detection of altered human DNA in stool: feasibility of a multitarget assay panel." Gastroenterology, 119: 1219-27.
Ahlquist et al., 2008, "Stool DNA and occult blood testing for screen detection of colorectal neoplasia." Ann Intern Med, 149: 441-50.
Allison et al., 2007, "Screening for colorectal neoplasms with new fecal occult blood tests: update on performance characteristics." J Natl Cancer Inst, 99: 1462-70.
De Kok, 2003, "Quantification and integrity analysis of DNA in the stool of colorectal cancer patients may represent a complex alternative to fecal occult blood testing." Clin Chem, 49: 2112-3.
Hardcastle et al., 1996, "Randomised controlled trial of faecal-occult-blood screening for colorectal cancer." Lancet, 348: 1472-7.
Nosho, et al. (2008): "PIK3CA mutation in colorectal cancer: Relationship with genetic and epigenetic alterations," Neoplasia. 10(6) 034-541, abstract only.
Harewood et al., 2000, "Fecal occult blood testing for iron deficiency: a reappraisal." Dig Dis, 18(2): 75-82.
Harewood et al., 2002, "Detection of occult upper gastrointestinal tract bleeding: performance differences in fecal occult blood tests." Mayo Clin Proc, 77: 23-28.
Heresbach et al., 2006, "Review in depth and meta-analysis of controlled trials on colorectal cancer screening by faecal occult blood test." Eur J Gastroenterol Hepatol, 18: 427-33.
Hoang et al., 1997, "BAT-26, an indicator of the replication error phenotype in colorectal cancers and cell lines." Cancer Res, 57: 300-3.
Imperiale et al., 2004, "Fecal DNA versus fecal occult blood for colorectal-cancer screening in an average-risk population." N Engl J Med, 351: 2704-14.
Jemal et al., 2007, "Cancer statistics, 2007." CA Cancer J Clin, 57: 43-66.
Kariya et al., 1987, "Revision of consensus sequence of human Alu repeats—a review." Gene, 53: 1-10.
Kronborg et al., 1996, "Randomised study of screening for colorectal cancer with faecal-occult-blood test." Lancet, 348: 1467-71.
Kronborg et al., 2004, "Randomized study of biennial screening with a faecal occult blood test: results after nine screening rounds." Scand J Gastroenterol, 39: 846-51.
Levin et al., 2008, "Screening and surveillance for the early detection of colorectal cancer and adenomatous polyps, 2008: a joint guideline from the American Cancer Society, the US Multi-Society Task Force on Colorectal Cancer, and the American College of Radiology." CA Cancer J Clin, 58: 130-60.
Mandel et al., 1993, "Reducing mortality from colorectal cancer by screening for fecal occult blood. Minnesota Colon Cancer Control Study." N Engl J Med, 328: 1365-71.
Meissner, 2006, "Patterns of colorectal cancer screening uptake among men and women in the United States." Cancer Epidemiol Biomarkers Prev, 15: 389-94.
Muller et al., 2004, "Methylation changes in faecal DNA: a marker for colorectal cancer screening?" Lancet, 363: 1283-5.
Olson et al., 2005, "DNA stabilization is critical for maximizing performance of fecal DNA-based colorectal cancer tests." Diagn Mol Pathol, 14: 183-91.
Osborn et al., 2005, "Stool screening for colorectal cancer: molecular approaches." Gastroenterology, 128: 192-206.
Sambrook et al., 1989, Fritsch, E.F., Maniatis, T. (ed.), Molecular Cloning, Cold Spring Harbor Lab. Press, Cold Spring Harbor, N.Y.
Samowitz et al., 1999, "BAT-26 and BAT-40 instability in colorectal adenomas and carcinomas and germline polymorphisms." Am J Path, 154: 1637-41.
Schwartz et al., 1983, "The "HemoQuant" test: a specific and quantitative determination of heme (hemoglobin) in feces and other materials." Clin Chem, 29: 2061-7.
Schwartz et al., 1985, "Quantitative fecal recovery of ingested hemoglobin-heme in blood: comparisons by HemoQuant assay with ingested meat and fish." Gastroenterology, 89: 19-26.
Singh et al., 2006, "Risk of developing colorectal cancer following a negative colonoscopy examination: evidence for a 10-year interval between colonoscopies." JAMA, 295: 2366-73.
Winawer et al., 1993, "Screening for colorectal cancer with fecal occult blood testing and sigmoidoscopy." J Natl Cancer Inst, 85: 1311-8.
Zijlstra et al., 2002, "A quantitative analysis of rate-limiting steps in the metastatic cascade using human-specific real-time polymerase chain reaction." Cancer Res, 62: 7083-92.
Zou et al., 2006, "A sensitive method to quantify human long DNA in stool: relevance to colorectal cancer screening." Cancer Epidemiol Biomarkers Prev, 15: 1115-9.
Crespi et al. "Colorectal cancer: a spreading but preventable disease" European Journal of Oncology. vol. 13(1). Mar. 2008. pp. 21-32.
Abbaszadegan, "Stool-based DNA testing, a new noninvasive method for colorectal cancer screening, the first report from Iran," World Journal of gastroenterology: WJG, vol. 13, p. 1528-1533, 2007.
Young, "Fecal Immunochemical Tests (FIT) vs. Office-based guaiac fecal occult blood test (FOBT)," Practical Gastroenterology, Colorectal Cancer, series 3, p. 46-56, 2004.
Wang, "Gene expression profiles and molecular markers to predict recurrence of duke's B Colon Cancer," vol. 22, p. 1564-1571, 2004.
Meuwis, "Contribution of proteomics to colorectal cancer diagnosis," Acta Endoscopica, vol. 37, p. 295-303, including translation, 2007.
Zou et al. "High Detection Rates of Colorectal Neoplasia by Stool DNA Testing with a Novel Digital Melt Curve Assay," Gastroenterology, vol. 136, No. 2, Feb. 1, 2009, pp. 459-470.
Zou et al. "T2034 Stool DNA and Occult Blood for Detection of Colorectal Cancer: Complementary Markers," Gastroenterology, vol. 136, No. 5, May 1, 2009, p. A-625.
Uchida, et al. (1994), "Immunochemical detection of human lactoferrin in feces as a new marker for inflammatorygastrointestinal disorders and colon cancer," Clinical Biochemistry. 27(4)L 259-264, abstract only.
Guzinska-Ustymowicz et al., (2009), "Correlation between proliferation makers: PCNA, Ki-67, MCM-2 and antiapoptopic protein Bcl2 in colorectal cancer," Anticancer Research. 29:3049-3052.
Saitoh et al. (1995), "Intestinal protein loss and bleeding assessed by fecal hemoglobin, transferrin, albumin, and alpha-1-antitrypsin levels in patients with colorectal diseases," Digestion. 56(1): 67-75, abstract only.
Wittekind et al. (1986), "Localization of CEA, HCG, lysozyme, alpha-1-antitrypsin, and alpha-1-antichymotrypsin in gastric cancer and prognosis," Virchows Arch 409:715-724.

(56) References Cited

OTHER PUBLICATIONS

Tibble, et al. (2001), "Faecal capprotectin and faecal occult blood tests in the diagnosis of colorectal carcinoma and adenoma.," Gut. 49:402-408.

Melle, et al. (2005), "Discovery and identification of a-defensins as low abundant, tumor-derived serum markers in colorectal cancer," 129(1): 66-73 abstract only.

Melotte, et al., (Jul. 1, 2009): "N-myc downstream-regulated gene 4 (NDRG4): a candidate tumor suppressor gene and potential biomarker for colorectal cancer," J. Natl Cancer Inst 101: 916-927.

Wen, et al. (2006), "Frequence epigenetic silencing of the borne morphogenic protein 2 gene through methylation in gastic carcinomas," Onogene. 25:2666-2673.

Grutzmann, et al. (2008), "Sensitive detection of colorectal cancer in peripheral blood by septin—DNA methylation assay," PLoS ONE 3(11): e3759 which is 8 pages long.

Zou, et al. (2007), "Highly methylated genes in colorectal neoplasia: Implications for screening," Cancer Epidemilogy Biomarkers Prev. 16(12): 2686-2696.

\* cited by examiner

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
acgcctgtaa tcccagcact t        21

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
tcgcccaggc tggagtgca        19

METHODS FOR DETECTING COLORECTAL CANCER USING A DNA MARKER OF EXFOLIATED EPITHELIA AND A FECAL BLOOD MARKER

CROSS-REFERENCE TO RELATED APPLICATION

The present application is a continuation of U.S. patent application Ser. No. 13/072,047, filed Mar. 25, 2011, which claims priority to U.S. Provisional Patent Application No. 61/318,077, filed Mar. 26, 2010, each of which is incorporated by reference in its entirety.

FIELD OF THE INVENTION

The present invention provides methods and materials related to the detection of colorectal neoplasm-specific markers in or associated with a subject's stool sample. In particular, the present invention provides methods and materials for identifying mammals having a colorectal neoplasm by detecting the presence of exfoliated epithelial markers (e.g., human DNA, tumor assoicated gene alterations, tumor associated proteins) and blood markers (e.g., homoglobin, serum proteins) in a stool sample obtained from the mammal.

BACKGROUND OF THE INVENTION

Colorectal cancer remains a leading cause of death among the types of cancer (see, e.g., Jemal A, et al., CA Cancer J Clin. 2007, 57:43-66; herein incorporated by reference in its entirety). Although screening reduces colorectal cancer mortality (see, e.g., Mandel J S, et al., N Engl J Med. 1993, 328:1365-71; Hardcastle J D, et al., Lancet. 1996, 348:1472-7; Kronborg O, et al., Scand J Gastroenterol. 2004, 39:846-51; Winawer S J, et al., J Natl Cancer Inst. 1993, 85:1311-8; Singh H, et al., JAMA. 2006, 295:2366-73; each herein incorporated by reference in their entireties), observed reductions have been modest (see, e.g., Singh H, et al., JAMA. 2006; 295, 2366-73; Heresbach D, et al., Eur J Gastroenterol Hepatol. 2006, 18:427-33; each herein incorporated by reference in their entireties) and more than one half of adults in the United States have not received screening (see, e.g., Meissner H I, Cancer Epidemiol Biomarkers Prev. 2006, 15:389-94; herein incorporated by reference in its entirety). More accurate, user-friendly, and widely distributable tools to improve screening effectiveness, acceptability, and access are needed.

SUMMARY

Fecal long DNA originate from either the exfoliation of dysplastic cells or from the luminal hemorrhage or exudation of leukocytes. Previous reports have speculated that long DNA and occult blood in stool resulted from bleeding, and as such, speculated that fecal long DNA testing might be an alternative of fecal occult blood testing (see, e.g., de Kok J B, Clin Chem. 2003; 49:2112-2113; herein incorporated by reference in its entirety). Experiments conducted during preparation of the embodiments for the present invention, however, demonstrated that long DNA was a continuously measurable marker in stool, and occult blood was detectable only intermittently (see, e.g., Osborn N K, et al., Gastroenterology 2005; 128:192-206, Ahlquist D A, Cancer 1989; 63:1826-1830; each herein incorporated by reference in their entireties) thereby indicating that long DNA and occult blood were from different sources and, as such, were complementary markers for CRC detection. Experiments further demonstrated that long DNA and occult blood in stools provide a sensitive approach for the detection of colorectal cancer.

Accordingly, in certain embodiments, the present invention provides methods for detecting the presence of a colorectal neoplasm in a mammal. In some embodiments, the methods involve obtaining a stool sample from a mammal, detecting the presence or absence of one or more exfoliated epithelial markers specific for a colorectal neoplasm in or associated with the stool sample, and detecting the presence or absence of one or more fecal occult blood markers (e.g., specific for a colorectal neoplasm) in the stool sample. In some embodiments, detection of the presence of one or more exfoliated epithelial markers in the stool sample in combination with the presence of one or more fecal occult blood markers in the stool sample is indicative of a colorectal neoplasm in the mammal.

In some embodiments, the mammal is a human. In some embodiments, the colorectal neoplasm is premalignant. In some embodiments, the colorectal neoplasm is malignant.

The methods are not limited to particular exfoliated epithelial markers specific for a colorectal neoplasm. In some embodiments, the one or more colorectal neoplasm-specific nucleic acid markers include, for example, a gene having a point mutation, a gene reflecting microsatellite instability, a gene having aberrant methylation, and/or long DNA.

In some embodiments, a gene having a point mutation includes, but is not limited to, K-ras, APC (see, e.g., U.S. Pat. Nos. 5,352,775, 5,648,212, 5,691,454, 5,783,666, RE36,713, U.S. Pat, Nos. 6,114,124, 6,413,727, and RE38, 916; each herein incorporated by reference in their entireties), melanoma antigen gene, p53 (see, e.g., U.S. Pat. Nos. 5,362,623, 5,527,676, 5,955,263, 6,090,566, 6,245,515, 6,677,312, 6,800,617, 7,087,583, 7,267,955; each herein incorporated by reference in their entireties), BRAF, BAT26 and PIK3CA (see, e.g., U.S. patent application Ser. No. 10/591,347; herein incorporated by reference in its entirety). In some embodiments, a gene reflecting microsatellite instability is BAT26. In some embodiments, a gene having aberrant methylation includes, but is not limited to, bmp-3, bmp-4, SFRP2, vimentin (see, e.g., U.S. Pat. No. 7,485,402; herein incorporated by reference in its entirety), septin9, ALX4, EYA4, TFPI2, NDRG4, HLTF (see, e.g., U.S. Pat. No. 7,432,050; herein incorporated by reference in its entirety), and FOXE1. In some embodiments, the long DNA is, for example, greater than 250 base pairs in length, greater than 300 base pairs in length, greater than 400 base pairs in length, greater than 500 base pairs in length, and/or greater than 1000 base pairs in length.

The methods are not limited to particular fecal occult blood markers specific for a colorectal neoplasm. In some embodiments, fecal occult blood markers specific for a colorectal neoplasm include, but are not limited to, hemoglobin, alpha-defensin, calprotectin, α1-antitrypsin, albumin, MCM2, transferrin, lactoferrin, and lysozyme.

In some embodiments, the exfoliated epithelial marker specific for colorectal neoplasm is long DNA, and the fecal occult blood marker specific for colorectal neoplasm is hemoglobin.

In some embodiments wherein a colorectal neoplasm is detected, additional techniques are performed to characterise the colorectal neoplasm (e.g., to characterize the colorectal neoplasm as malignant or premalignant) (e.g., to characterize the colorectal neoplasm within a particular stage of colorectal cancer).

In certain embodiments, the present invention provides kits for detecting the presence of a colorectal neoplasm in a mammal. In some embodiments, such kits include reagents useful, sufficient, or necessary for detecting and/or characterizing one or more exfoliated epithelial markers specific for a colorectal neoplasm, and reagents useful, sufficient, or necessary for detecting and/or characterizing one or more fecal occult blood markers specific for a colorectal neoplasm. In some embodiments, the kits contain the reagents necessary to perform real-time Alu PCR. In some embodiments, the kits contain the reagents necessary to perform the heme porphyrin test HemoQuant. In some embodiments, the kits contain the ingredients and reagents necessary to obtain and store a stool sample from a subject.

In certain embodiments, the present invention provides methods for monitoring the treatment of colorectal cancer. For example, in some embodiments, the methods may be performed immediately before, during and/or after a treatment to monitor treatment success. In some embodiments, the methods are performed at intervals on disease free patients to insure or monitor treatment success.

In certain embodiments, the present invention provides methods for obtaining a subject's risk profile for developing colorectal cancer. In some embodiments, such methods involve obtaining a stool sample from a subject (e.g., a human at risk for developing colorectal cancer; a human undergoing a routine physical examination), detecting the presence or absence of one or more exfoliated epithelial markers specific for a colorectal neoplasm in or associated with the stool sample, detecting the presence or absence of one or more fecal occult blood markers (e.g., specific for a colorectal neoplasm) in or associated with the stool sample, and generating a risk profile for developing colorectal cancer based upon the detected presence or absence of the exfoliated epithelial markers and fecal occult blood markers. For example, in some embodiments, a generated risk profile will change depending upon specific exfoliated epithelial markers and fecal occult blood markers detected as present or absent. The present invention is not limited to a particular manner of generating the risk profile. In some embodiments, a processor (e.g., computer) is used to generate such a risk profile. In some embodiments, the processor uses an algorithm (e.g., software) specific for interpreting the presence and absence of specific exfoliated epithelial markers and fecal occult blood markers as determined with the methods of the present invention. In some embodiments, the presence and absence of specific exfoliated epithelial markers and fecal occult blood markers as determined with the methods of the present invention are inputed into such an algorithm, and the risk profile is reported based upon a comparison of such input with established norms (e.g., established norm for pre-cancerous condition, established norm for various risk levels for developing colorectal cancer, established norm for subjects diagnosed with various stages of colorectal cancer). In some embodiments, the risk profile indicates a subject's risk for developing colorectal cancer or a subject's risk for re-developing colorectal cancer. In some embodiments, the risk profile indicates a subject to be, for example, at a very low, a low, a moderate, a high, and a very high chance of developing or re-developing colorectal cancer. In some embodiments, the risk profile indicates risk based on a population average at a desired level of specificity (e.g., 90%). In some embodiments, a health care provider (e.g., an oncologist) will use such a risk profile in determining a course of treatment or intervention (e.g., colonoscopy, wait and see, referral to an oncologist, referral to a surgeon, etc.).

DEFINITIONS

Figure 1A:
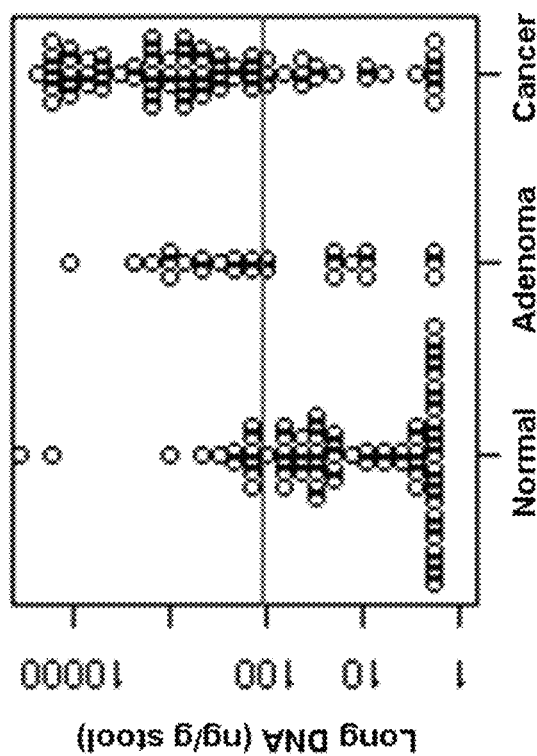
FIG. 1A-B shows the levels of long DNA and occult blood in stools from patients with CRCs or advanced adenomas and from normal individuals displayed in log scale. Each circle represents one stool sample.

To facilitate an understanding of the present invention, a number of terms and phrases are defined below As used herein, the term "colorectal cancer" is meant to include the well-accepted medical definition that defines colorectal cancer as a medical condition characterized by cancer of cells of the intestinal tract below the small intestine (e.g., the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum).

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. As used herein, the term "metastasized colorectal cancer cells" is meant to refer to colorectal cancer cells which have metastasized; colorectal cancer cells localized in a part of the body other than the duodenum, small intestine (jejunum and ileum), large intestine (colon), including the cecum, ascending colon, transverse colon, descending colon, and sigmoid colon, and rectum.

As used herein, "an individual is suspected of being susceptible to metastasized colorectal cancer" is meant to refer to an individual who is at an above-average risk of developing metastasized colorectal cancer. Examples of individuals at a particular risk of developing metastasized colorectal cancer are those whose family medical history indicates above average incidence of colorectal cancer among family members and/or those who have already developed colorectal cancer and have been effectively treated who therefore face a risk of relapse and recurrence. Other factors which may contribute to an above-average risk of developing metastasized colorectal cancer which would thereby lead to the classification of an individual as being suspected of being susceptible to metastasized colorectal cancer may be based upon an individual's specific genetic, medical and/or behavioral background and characteristics.

The term "neoplasm" as used herein refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells. The term "colorectal neoplasm-specific marker" refers to any biological material that can be used to indicate the presence of a colorectal neoplasm (e.g., a premalignant colorectal neoplasm; a malignant colorectal neoplasm). Examples of colorectal neoplasm-specific markers include, but are not limited to, exfoliated epithelial markes (e.g., bmp-3, bmp-4, SFRP2, vimentin, septin9, ALX4, EYA4, TFPI2, NDRG4, FOXE1, long DNA, BAT-26, K-ras, APC, melanoma antigen gene, p53, BRAF, and PIK3CA) and fecal occult blood markers (e.g., hemoglobin, alpha-defensin, calprotectin, α1-antitrypsin, albumin, MCM2, transferrin, lactoferrin, and lysozyme).

As used herein, the term "adenoma" refers to a benign tumor of glandular origin. Although these growths are benign, over time they may progress to become malignant. As used herein the term "colorectal adenoma" refers to a benign colorectal tumor in which the cells form recognizable glandular structures or in which the cells are clearly derived from glandular epithelium.

As used herein, the term "amplicon" refers to a nucleic acid generated using primer pairs. The amplicon is typically single-stranded DNA (e.g., the result of asymmetric amplification), however, it may be RNA or dsDNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), Hot-start PCR (see, e.g., U.S. Pat. Nos. 5,773,258 and 5,338,671; each herein incorporated by reference in their entireties), intersequence-specfic PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, etl al., (1992) Biotechnology 10:413-417; Higuchi, et al., (1993) Biotechnology 11:1026-1030; each of which are herein incorporated by reference in their entireties), reverse transcription PCR (see, e.g., Bustin, S.A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

DETAILED DESCRIPTION OF THE INVENTION

An effective way to detect colorectal cancer (CRC) at early stages is population screening. Colonoscopy and fecal occult blood testing (FOBT) are commonly used tools for CRC screening, but the adherent rates of both approaches are low due to the invasiveness and expense of colonoscopy and the low sensitivity of FOBT (see, e.g., Osborn N K, et al., Gastroenterology 2005; 128:192-206; Levin B, et al., CA Cancer J Clin 2008; 58:130-160; each herein incorporated by reference in its entirety). For example, fecal long DNA quantified with real-time Alu PCR is a simple approach for CRC detection, but its sensitivity is less optimal when assayed alone (see, e.g., Zou H, et al., Cancer Epidemiol Biomarkers Prev 2006; 15:1115-1119; herein incorporated by reference in its entirety).

Fecal long DNA originate from either the exfoliation of dysplastic cells or from the luminal hemorrhage or exudation of leukocytes. Previous reports have speculated that long DNA and occult blood in stool resulted from bleeding, and as such, speculated that fecal long DNA testing might be an alternative of fecal occult blood testing (see, e.g., de Kok J B, Clin Chem. 2003; 49:2112-2113; herein incorporated by reference in its entirety). Experiments conducted during preparation of the embodiments for the present invention, however, demonstrated that long DNA was a continuously measurable marker in stool, and occult blood was detectable only intermittently (see, e.g., Osborn N K, et al., Gastroenterology 2005; 128:192-206, Ahlquist D A, Cancer 1989; 63:1826-1830; each herein incorporated by reference in their entireties) thereby indicating that long DNA and occult blood were from different sources and, as such, were complementary markers for CRC detection. Experiments further demonstrated that long DNA and occult blood in stools provide a sensitive approach for the detection of colorectal cancer.

Ideally, approaches for screening colorectal cancer should be accurate, user friendly, and inexpensive. Both fecal long DNA and occult blood testings are simple non-invasive approaches, but their sensitivities for CRC detection are less optimal when assayed alone (see, e.g., Zou H, et al., Cancer Epidemiol Biomarkers Prey 2006; 15:1115-1119; Mandel J S, et al., N Engl J Med 1993; 328:1365-1371; Kronborg O, et al., Lancet 1996; 348:1467-1471; Hardcastle J D, et al., Lancet 1996; 348:1472-1477; Ahlquist D A, et al., JAMA 1993; 269:1262-1267; Imperiale T F, et al., N Engl J Med 2004; 351:2704-2714; Ahlquist D A, Ann Intern Med 2008; 149:441-450; Ahlquist D A, Gastroenterology 2000; 119: 1219-1227; each herein incorporated by reference in their entireties). As experiments conducted during preparation of the embodiments for the present invention demonstrated that stool based long DNA and fecal occult blood are complementary markers originating from different sources, the present invention, in some embodiments, provides a quantitative assay combining exfoliated epithelial markers (e.g., long DNA) and fecal occult blood markers (e.g., hemoglobin) yielding an inexpensive approach for sensitive detection of CRC.

Accordingly, the present invention provides methods and materials related to the detection of colorectal cancer-specific markers in a subject's stool sample. In particular, the present invention provides methods and materials for identifying mammals having a colorectal cancer by detecting the presence of exfoliated epithelial markers (e.g., human long DNA, tumor assoicated gene alterations, tumor associated proteins) and fecal occult blood markers (e.g., hemoglobin, serum proteins) in a stool sample obtained from the mammal.

While the present invention exemplifies several markers specific for detecting colorectal cancer, any marker that is correlated with the presence or absence of colorectal cancer may be used. A marker, as used herein, includes, for example, any proteinaceous molecule (or corresponding gene) whose production or lack of production is characteristic of a colorectal cancer cell. Depending on the particular set of markers employed in a given analysis, the statistical analysis will vary. For example, where a particular combination of markers is highly specific for colorectal cancer, the statistical significance of a positive result will be high. It may be, however, that such specificity is achieved at the cost of sensitivity (e.g., a negative result may occur even in the presence of colorectal cancer). By the same token, a different combination may be very sensitive (e.g., few false negatives, but has a lower specificity).

Particular combinations of markers may be used that show optimal function with different ethnic groups or sex, different geographic distributions, different stages of disease, different degrees of specificity or different degrees of sensitivity. Particular combinations may also be developed which are particularly sensitive to the effect of therapeutic regimens on disease progression. Subjects may be monitored after a therapy and/or course of action to determine the effectiveness of that specific therapy and/or course of action.

As noted, experiments conducted during the course of developing embodiments for the present invention determined an enhanced method and system for detecting colorectal cancer through detecting and assessing both the presence or absence of exfoliated epithelial markers (e.g., human DNA, tumor assoicated gene alterations, tumor associated proteins) and fecal occult blood markers (e.g., hemoglobin, serum proteins) in a stool sample obtained from the mammal.

The present invention is not limited to detecting particular exfoliated epithelial markers specific for detecting colorectal cancer. In some embodiments, the exfoliated epithelial markers specific for detecting colorectal cancer include nucleic acid. Examples of colorectal cancer-specific nucleic acid markers include, without limitation, nucleic acid having a point mutation, nucleic acid that reflects microsatellite instability, nucleic acid having aberrrant methylation, and long DNA.

Nucleic acid having a point mutation can encode a polypeptide or regulate the expression of a polypeptide (e.g., promoters, enhancers, and silencers). Examples of nucleic acid that can contain a point mutation indicative of a colorectal cancer include, without limitation, the genes for K-ras, APC (adenomatous polyposis coli), melanoma antigen gene, p53, BRAF, BAT26, and PIK3CA.

Nucleic acid that reflects microsatellite instability can be used to indicate the presence of colorectal cancer. Briefly, nucleic acid that reflects microsatellite instability can be identified as described elsewhere (see, e.g., Samowitz et al., Am. J. Path., 154:1637-1641 (1999); Hoang et al., Cancer Res., 57:300-303 (1997); each herein incorporated by reference in its entirety). An example of nucleic acid that can reflect microsatellite instability indicative of a colorectal neoplasm includes, without limitation, the gene for BAT-26.

Nucleic acid having aberrant methylation can be used to indicate the presence of colorectal cancer (see, e.g., Muller, et al., Lancet 2004 363:1283-1285; herein incorporated by reference in its entirety). Examples of nucleic acid having aberrant methylation indicative of colorectal cancer include, but are not limited to, bmp-3, bmp-4, SFRP2, vimentin, septin9, ALX4, EYA4, TFPI2, NDRG4, and FOXE1.

The presence of long DNA in a stool sample is indicative of colorectal cancer. Long DNA is a marker for non-apoptotic cells. Typically, cells shed from normal mucosa are apoptotic, while those shed from colorectal neoplasms are non-apoptotic. As described herein, long DNA can be used as a colorectal cancer-specific marker for subjects having colorectal cancer. One hallmark of apoptosis is the autodigestion or cleavage of DNA into "short" fragments of about 180 base-pairs. The detection of "long" DNA (e.g., DNA greater than about 200 base-pairs) in a stool sample can indicate the presence of non-apoptotic cells of neoplastic lineage derived from a colorectal neoplasm. The term "long DNA" as used herein refers to DNA greater than about 200 base-pairs (e.g., greater than about 250, 300, 350, 400, 500, 600, 700, 800, 900, 1000, 1250, 1500, 1750, 2000, or 2500 base-pairs).

The present invention is not limited to a particular method for detecting and/or quanitifying long DNA within a subject's stool sample. In some embodiments, real-time Alu PCR is used for detecting and/or quanitifying long DNA within a subject's stool sample. Real-time Alu PCR is a sensitive method for detecting non-apoptotic human DNA in stool as it targets abundant Alu repeats in human genome (see, e.g., Zou H, et al. Cancer Epidemiol Biomarkers Prev 2006, 15:1115-1119; herein incorporated by reference in its entirety). Alu sequences embody the largest family of middle repetitive DNA sequences in human genome (see, e.g., Kariya Y, et al., Gene 1987, 53:1-10; herein incorporated by reference in its entirety). An estimated half million Alu copies are present per haploid human genome (see, e.g., Kariya Y, et al., Gene 1987, 53:1-10; herein incorporated by reference in its entirety). Accordingly, as Alu sequences are so abundantly distributed throughout the genome and specific to the genomes primates, real-time Alu PCR amplifies DNA sequences longer than 200 bp within these 300-bp repeats (see, e.g., Kariya Y, et al., Gene 1987, 53:1-10; herein incorporated by reference in its entirety) thereby providing a genome-wide approach to quantify human long DNA in stool (see, e.g., Zou H, et al. Cancer Epidemiol Biomarkers Prev 2006, 15:1115-1119; herein incorporated by reference in its entirety).

The present invention is not limited to detecting particular fecal occult blood markers specific for colorectal cancer. In some embodiments, the fecal occult blood markers specific for detecting colorectal neoplasm include, without limitation, hemoglobin, alpha-defensin, calprotectin, α1-antitrypsin, albumin, MCM2, transferrin, lactoferrin, and lysozyme.

Any fecal occult blood testing method can be used to detect colorectal cancer-specific fecal occult blood markers. For example, antibodies specific for a polypeptide marker can be used in an immunoassay (e.g., ELISA) to detect the presence or absence of the polypeptide in a stool sample that is indicative of the presence of colorectal cancer. To accurately evaluate bleeding in the digestive tract, it is important that fecal occult blood tests target analytes that are stable during the enteric transit. Available data indicate that both guaiac and immunochemical FOBTs are insensitive for the detection of bleeding from proximal colon (see, e.g., Imperiale, et al., N Engl J Med 2004, 351:2704-2714; Ahlquist, et al., Ann Intern Med 2008, 149:441-450; Harewood, et al., Mayo Clin Proc 2002, 77:23-28; Allison, et al., J Natl Cancer Inst 2007, 99:1462-1470; each herein incorporated by reference in their entireties). In contrast, the heme porphyrin test HemoQuant is sensitive for both proximal and distal sources of occult bleeding (see, e.g., Harewood, et al., Mayo Clin Proc 2002, 77:23-28; Ahlquist, et al., N Engl J Med 1985, 312:1422-1428; Harewood, et al., Dig Dis. 2000, 18(2):75-82; each herein incorporated by reference in their entireties). Accordingly, in some embodiments, the heme porphyrin test HemoQuant is used for detecting and/or quantifying the colorectal cancer-specific fecal occult blood marker hemoglobin.

The present invention is not limited to a particular combination of exfoliated epithelial markers and fecal occult blood markers in the detection of colorectal cancer in a subject. In some embodiments, any one or more exfoliated epithelial markers are used (e.g., bmp-3, bmp-4, SFRP2, vimentin, septin9, ALX4, EYA4, TFPI2, NDRG4, FOXE1, long DNA, BAT-26, K-ras, APC, melanoma antigen gene, p53, BRAF, and PIK3CA). In some embodiments, any one or more fecal occult blood markers are used (e.g., hemoglobin, alpha-defensin, calprotectin, α1-antitrypsin, albumin, MCM2, transferrin, lactoferrin, and lysozyme).

It is noted that a single stool sample can be analyzed for one colorectal neoplasm-specific marker or for multiple colorectal neoplasm-specific markers. For example, a stool sample can be analyzed using assays that detect a panel of different colorectal neoplasm-specific markers. In addition, multiple stool samples can be collected for a single mammal and analyzed as described herein. Indeed, U.S. Pat. Nos. 5,670,325, 5,741,650, 5,928,870, 5,952,178, and 6,020,137, each herein incorporated by reference in their entireties, for example, describe various methods that can be used to prepare and analyze stool samples. In some embodiments, a stool sample is split into first and second portions, where the first portion undergoes analysis for exfoliated epithelial markers and the second portion undergoes analysis for fecal occult blood markers. In some embodiments, the stool sample undergoes one or more preprocessing steps before being split into portions.

The present invention is not limited to a particular manner of detecting nucleic acid markers corresponding to colorectal neoplasm from a stool sample. In some embodiments, nucleic acid is amplified. Generally, nucleic acid used as template for amplification is isolated from cells contained in the biological sample according to standard methodologies (see, e.g., Sambrook, J., et al., Fritsch, E. F., Maniatis, T. (ed.). MOLECULAR CLONING. Cold Spring Harbor Lab. Press, Cold Spring Harbor, N.Y. (1989); herein incorporated by reference in its entirety). The nucleic acid may be genomic DNA or fractionated or whole cell RNA. Where RNA is used, it may be desired to convert the RNA to a complementary cDNA. In a preferred embodiment, the RNA is whole cell RNA and is used directly as the template for amplification. Pairs of primers that selectively hybridize to genes corresponding to specific markers are contacted with the isolated nucleic acid under conditions that permit selective hybridization. Once hybridized, the nucleic acid primer complex is contacted with one or more enzymes that facilitate template-dependent nucleic acid synthesis. Multiple rounds of amplification, also referred to as "cycles," are conducted until a sufficient amount of amplification product is produced. Next, the amplification product is detected. In some applications, the detection may be performed by visual means. Alternatively, the detection may involve indirect identification of the product via chemiluminescence, radioactive scintigraphy of incorporated radio label or fluorescent label or even via a system using electrical or thermal impulse signals. Generally, the foregoing process is conducted at least twice on a given sample using at least two different primer pairs specific for two different specific markers. Following detection, in some embodiments, the results seen in a given subject are compared with a statistically significant reference group of subjects diagnosed as not having colorectal cancer.

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

In most cases, it will be preferable to synthesize desired oligonucleotides. Suitable primers can be synthesized using commercial synthesizers using methods well known to those of ordinary skill in the art. Where double-stranded primers are desired, synthesis of complementary primers is performed separately and the primers mixed under conditions permitting their hybridization.

Selection of primers is based on a variety of different factors, depending on the method of amplification and the specific marker involved. For example, the choice of primer will determine the specificity of the amplification reaction. The primer needs to be sufficiently long to specifically hybridize to the marker nucleic acid and allow synthesis of amplification products in the presence of the polymerization agent and under appropriate temperature conditions. Shorter primer molecules generally require cooler temperatures to form sufficiently stable hybrid complexes with the marker nucleic acid and may be more susceptible to non-specific hybridization and amplification.

Primer sequences do not need to correspond exactly to the specific marker sequence. Non-complementary nucleotide fragments may be attached to the 5' end of the primer with the remainder of the primer sequence being complementary to the template. Alternatively, non-complementary bases can be interspersed into the primer, provided that the primer sequence has sufficient complementarily, in particular at the 3' end, with the template for annealing to occur and allow synthesis of a complementary DNA strand.

In some embodiments, primers may be designed to hybridize to specific regions of the marker nucleic acid sequence. For example, GC rich regions are favored as they form stronger hybridization complexes than AT rich regions. In another example, primers are designed, solely, to hybridize to a pair of exon sequences, with at least one intron in between. This allows for the activity of a marker gene to be detected as opposed to its presence by minimizing background amplification of the genomic sequences and readily distinguishes the target amplification by size.

Primers also may be designed to amplify a particular segment of marker nucleic acid that encodes restriction sites. A restriction site in the final amplification product would enable digestion at that particular site by the relevant restriction enzyme to produce two products of a specific size. Any restriction enzyme may be utilized in this aspect. This added refinement to the amplification process may be necessary when amplifying a marker nucleic acid sequence with close sequence similarity to other nucleic acids. Alternatively, it may be used as an added confirmation of the specificity of the amplification product.

A number of template dependent processes are available to amplify the marker sequences present in a given template sample. One of the best known amplification methods is the polymerase chain reaction (PCR) (see, e.g., U.S. Pat. Nos. 4,683,195, 4,683,202, 4,800,159, and Innis et al., PCR Protocols, Academic Press, Inc., San Diego, Calif. (1990); each incorporated herein by reference in their entireties). Briefly, in PCR, two primer sequences are prepared which are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated. In some embodiments, a reverse transcriptase PCR amplification procedure is performed in order to quantify the amount of mRNA amplified. Methods of reverse transcribing RNA into cDNA are well known (see, e.g., Sambrook, J., et al., Fritsch, E. F., Maniatis, T. (ed.). MOLECULAR CLONING. Cold Spring Harbor Lab. Press, Cold Spring Harbor, N.Y. (1989); herein incorporated by reference in its entirety). Alternatively, methods for reverse transcription utilize thermostable DNA polymerases (see, e.g., WO 90/07641; herein incorporated by reference in its entirety).

The present invention is not limited to a particular PCR technique. Examples of PCR include, but are not limited to, standard PCR, allele-specific PCR, assembly PCR, asymmetric PCR, digital PCR, helicase-dependent amplification, Hot-start PCR, interseqeunce-specfic PCR, inverse PCR, ligation-mediated PCR, methylation-specific PCR, miniprimer PCR, multiplex ligation-dependent probe amplification, nested PCR, overlap-extension PCR, real-time PCR, reverse transcription PCR, solid phase PCR, thermal asymmetric interlaced PCR, and Touchdown PCR.

Another method for amplification is the ligase chain reaction ("LCR") (see, e.g., U.S. Pat. Nos. 4,883,750 and 5,494,810; herein incorporated by reference in its entirety). In LCR, two complementary probe pairs are prepared, and in the presence of the marker sequence, each pair will bind to opposite complementary strands of the marker such that they abut. In the presence of a ligase, the two probe pairs will link to form a single unit. By temperature cycling, as in PCR, bound ligated units dissociate from the marker and then serve as "target sequences" for ligation of excess probe pairs.

Following amplification, it may be desirable to separate the amplification product from the template and the excess primer for the purpose of determining whether specific amplification occurred. In some embodiments, amplification products are separated by agarose, agarose-acrylamide or polyacrylamide gel electrophoresis using standard methods (see, e.g., Sambrook, J., et al., Fritsch, E. F., Maniatis, T. (ed.). MOLECULAR CLONING. Cold Spring Harbor Lab. Press, Cold Spring Harbor, N.Y. (1989); herein incorporated by reference in its entirety).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (see, e.g., Freifelder, D. Phpysical Biochemistry Applications to Biochemistry and Molecular Biology. 2nd ed. Wm. Freeman & Co., New York, N.Y. 1982; incorporated herein by reference in its entirety).

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In some embodiments, visualization is achieved indirectly. For example, following separation of amplification products, a nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In some embodiments, detection is by Southern blotting and hybridization with a labeled probe. The techniques involved in Southern blotting are well known to those of skill in the art and can be found in many standard books on molecular protocols (see, e.g., Sambrook, J., et al., Fritsch, E. F., Maniatis, T. (ed.). MOLECULAR CLONING. Cold Spring Harbor Lab. Press, Cold Spring Harbor, N.Y. (1989); herein incorporated by reference in its entirety). Briefly, amplification products are separated by gel electrophoresis. The gel is then contacted with a membrane, such as nitrocellulose, permitting transfer of the nucleic acid and noncovalent binding. Subsequently, the membrane is incubated with a chromophore conjugated probe that is capable of hybridizing with a target amplification product. Detection is by exposure of the membrane to x-ray film or ion-emitting detection devices.

In some embodiments, all the basic essential materials and reagents required for detecting colorectal cancer through detecting both the presence or absence of exfoliated epithelial markers (e.g., human DNA, tumor assoicated gene alterations, tumor associated proteins) and fecal occult blood markers (e.g., hemoglobin, serum proteins) in a stool sample obtained from the mammal are assembled together in a kit. Such kits generally comprise, for example, reagents useful, sufficient, or necessary for detecting and/or characterizing one or more exfoliated epithelial markers specific for a colorectal neoplasm (e.g., bmp-3, bmp-4, SFRP2, vimentin, septin9, ALX4, EYA4, TFPI2, NDRG4, FOXE1, long DNA, BAT-26, K-ras, APC, melanoma antigen gene, p53, BRAF, and PIK3CA), and reagents useful, sufficient, or necessary for detecting and/or characterizing one or more fecal occult blood markers specific for a colorectal neoplasm (e.g., hemoglobin, alpha-defensin, calprotectin, α1-antitrypsin, albumin, MCM2, transferrin, lactoferrin, and lysozyme). In some embodiments, the kits contain enzymes suitable for amplifying nucleic acids including various polymerases, deoxynucleotides and buffers to provide the necessary reaction mixture for amplification. In some embodiments, the kits contain reagents necessary to perform Real-time Alu PCR. In some embodiments, the kits contain reagents necessary to perform the heme porphyrin test HemoQuant. In some embodiments, the kits of the present invention include a means for containing the reagents in close confinement for commercial sale such as, e.g., injection or blow-molded plastic containers into which the desired reagent are retained. Other containers suitable for conducting certain steps of the disclosed methods also may be provided.

In some embodiments, the methods disclosed herein are useful in monitoring the treatment of colorectal cancer. For example, in some embodiments, the methods may be performed immediately before, during and/or after a treatment to monitor treatment success. In some embodiments, the methods are performed at intervals on disease free patients to insure treatment success.

The present invention also provides a variety of computer-related embodiments. Specifically, in some embodiments the invention provides computer programming for analyzing and comparing a pattern of colorectal neoplasm-specific marker (e.g., exfoliated epithelial markers and fecal occult blood markers) detection results in a stool sample obtained from a subject to, for example, a library of such marker patterns known to be indicative of the presence or absence of a colorectal cancer, or a particular stage or colorectal cancer.

In some embodiments, the present invention provides computer programming for analyzing and comparing a first and a second pattern of colorectal neoplasm-specific marker (e.g., exfoliated epithelial markers and fecal occult blood markers) detection results from a stool sample taken at least two different time points. In some embodiments, the first pattern may be indicative of a pre-cancerous condition and/or low risk condition for colorectal cancer and/or progression from a pre-cancerous condition to a cancerous condition. In such embodiments, the comparing provides for monitoring of the progression of the condition from the first time point to the second time point.

In yet another embodiment, the invention provides computer programming for analyzing and comparing a pattern of colorectal neoplasm-specific marker (e.g., exfoliated epithelial markers and fecal occult blood markers) detection results from a stool sample to a library of colorectal neoplasm-specific marker patterns known to be indicative of the presence or absence of a colorectal cancer, wherein the comparing provides, for example, a differential diagnosis between a benign colorectal neoplasm, and an aggressively malignant colorectal neoplasm (e.g., the marker pattern provides for staging and/or grading of the cancerous condition).

The methods and systems described herein can be implemented in numerous ways. In one embodiment, the methods involve use of a communications infrastructure, for example the internet. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of colorectal neoplasm-specific marker (e.g., exfoliated epithelial markers and fecal occult blood markers) detection results from a stool sample). This information received can be stored at least temporarily in a database, and data analyzed in comparison to a library of marker patterns known to be indicative of the presence or absence of a pre-cancerous condition, or known to be indicative of a stage and/or grade of colorectal cancer.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In some embodiments, all or a portion of the input data and/or all or a portion of the output data (e.g., usually at least the library of the pattern of colorectal neoplasm-specific marker (e.g., exfoliated epithelial markers and fecal occult blood markers) detection results known to be indicative of the presence or absence of a pre-cancerous condition) are maintained on a server for access, e.g., confidential access. The results may be accessed or sent to professionals as desired.

A system for use in the methods described herein generally includes at least one computer processor (e.g., where the method is carried out in its entirety at a single site) or at least two networked computer processors (e.g., where detected marker data for a stool sample obtained from a subject is to be input by a user (e.g., a technician or someone performing the activity assays)) and transmitted to a remote site to a second computer processor for analysis (e.g., where the pattern of colorectal neoplasm-specific marker (e.g., exfoliated epithelial markers and fecal occult blood markers) detection results is compared to a library of patterns known to be indicative of the presence or absence of a pre-cancerous condition), where the first and second computer processors are connected by a network, e.g., via an intranet or internet). The system can also include a user component(s) for input; and a reviewer component(s) for review of data, and generation of reports, including detection of a pre-cancerous condition, staging and/or grading of a colorectal neoplasm, or monitoring the progression of a pre-cancerous condition or a colorectal neoplasm. Additional components of the system can include a server component(s); and a database(s) for storing data (e.g., as in a database of report elements, e.g., a library of marker patterns known to be indicative of the presence or absence of a pre-cancerous condition and/or known to be indicative of a grade and/or a stage of a colorectal neoplasm, or a relational database (RDB) which can include data input by the user and data output. The computer processors can be processors that are typically found in personal desktop computers (e.g., IBM, Dell, Macintosh), portable computers, mainframes, minicomputers, or other computing devices.

The input components can be complete, stand-alone personal computers offering a full range of power and features to run applications. The user component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

In certain embodiments, the present invention provides methods for obtaining a subject's risk profile for developing colorectal cancer. In some embodiments, such methods involve obtaining a stool sample from a subject (e.g., a human at risk for developing colorectal cancer; a human undergoing a routine physical examination), detecting the presence or absence of one or more exfoliated epithelial markers specific for a colorectal neoplasm in or associated with the stool sample, detecting the presence or absence of one or more fecal occult blood markers (e.g., specific for a colorectal neoplasm) in or associated with the stool sample, and generating a risk profile for developing colorectal cancer based upon the detected presence or absence of the exfoliated epithelial markers and fecal occult blood markers. For example, in some embodiments, a generated risk profile will change depending upon specific exfoliated epithelial markers and fecal occult blood markers detected as present or absent. The present invention is not limited to a particular manner of generating the risk profile. In some embodiments, a processor (e.g., computer) is used to generate such a risk profile. In some embodiments, the processor uses an algorithm (e.g., software) specific for interpreting the presence and absence of specific exfoliated epithelial markers and fecal occult blood markers as determined with the methods of the present invention. In some embodiments, the presence and absence of specific exfoliated epithelial markers and fecal occult blood markers as determined with the methods of the present invention are inputed into such an algorithm, and the risk profile is reported based upon a comparison of such input with established norms (e.g., established norm for pre-cancerous condition, established norm for various risk levels for developing colorectal cancer, established norm for subjects diagnosed with various stages of colorectal cancer). In some embodiments, the risk profile indicates a subject's risk for developing colorectal cancer or a subject's risk for re-developing colorectal cancer. In some embodiments, the risk profile indicates a subject to be, for example, a very low, a low, a moderate, a high, and a very high chance of developing or re-developing colorectal cancer. In some embodiments, the risk profile indicates risk based on a population average at a desire level of specificity (e.g., 90%). In some embodiments, a health care provider (e.g., an oncologist) will use such a risk profile in determining a course of treatment or intervention (e.g., colonoscopy, wait and see, referral to an oncologist, referral to a surgeon, etc.).

EXAMPLES

The invention now being generally described, will be more readily understood by reference to the following example, which is included merely for purposes of illustration of certain aspects and embodiments of the present invention, and are not intended to limit the invention.

Example 1

Subjects

A total of two hundred and one subjects, including 74 patients with CRC, 27 with advanced adenoma (≥1cm), and 100 colonoscopically normal individuals, were all recruited. Their demographic and clinical characteristics are described in Table 1.

TABLE 1

Demographic and clinical characteristics of subjects

|  | Colorectal cancer | Advanced adenoma | Normal control |
|---|---|---|---|
| Number | 74 | 27 | 100 |
| Median Age (Range) | 61 (40-87) yrs | 67 (50-82) yrs | 59 (28-81) yrs |
| Sex (Male/Female) | 52/22 | 15/12 | 37/63 |
| Site (Right/Left) | 29/45 | 17/10 |  |
| Stage (I/II/III/IV) | 13/16/27/18 |  |  |
| Grade (1/2/3/4) or Dysplasia (Low/High) | 0/4/55/5 | 20/5 |  |

Stool Collection

Stools were collected more than 2 weeks following any colorectal diagnostic procedure or cathartic preparation and prior to either endoscopic or surgical neoplasm resection. Patients collected whole stools in a preservative buffer (0.5 mol/L Tris, 10 mmol/L NaCl, 150 mmol/L EDTA, pH 9.0) as described (see, e.g., Olson J, et al., Diagn Mol Pathol 2005; 14:183-191; herein incorporated by reference in its entirety), and mailed to a laboratory within 48 hours. Once a stool arrived in the laboratory, it was weighed and homogenized. One aliquot equivalent to 10 g stool was used for stool DNA extraction, and the rest was stored at −80° C. in aliquots.

Long DNA Quantification With Real-Time Alu PCR

Crude stool DNA was extracted with isopropanol, precipitated with ethanol, and eluted in 7.5 ml 1×TE buffer. Human DNA in crude stool DNA was quantified using a real-time Alu PCR method (see, e.g., Zou H, et al., Cancer Epidemiol Biomarkers Prey 2006; 15:1115-1119; herein incorporated by reference in its entirety). Primers specific for the human Alu sequences, sense: 5'-ACG CCT GTA ATC CCA GCA CTT-3; and antisense: 5'-TCG CCC AGG CTG GAG TGC A-3' were used to amplify sequences about 245 bp inside Alu repeats (see, e.g., Zou H, et al., Cancer Epidemiol Biomarkers Prey 2006; 15:1115-1119; Zijlstra A, et al., Cancer Res 2002; 62:7083-7092; each herein incorporated by reference in their entireties). Crude stool DNA was diluted 1 to 100 with nuclease-free water for PCR amplification. One µL water-diluted stool DNA was amplified in a total volume of 25 µL containing 1×iQ™ SYBR® Green Supermix (BioRad), 200 nM each primer under the following conditions: 95° C. for 3 minutes, followed by 30 cycles of 95° C. for 30 seconds, 60° C. for 30 seconds, and 72° C. for 40 seconds in a real-time iCycler® (BioRad). Standard curve was created for each plate by amplifying 10-fold serially diluted human genomic DNA samples (Novagen, Madison, Wis.). Melting curve was made after each PCR reaction to confirm that only one product was amplified for all samples. Amplification was carried out in 96-well plates. Each plate consisted of stool DNA samples and multiple positive and negative controls. Each assay was performed in duplicate.

Fecal Occult Blood Quantification With HemoQuant

Fecal occult blood was quantified with HemoQuant test (see, e.g., Harewood G C, et al., Mayo Clin Proc 2002; 77:23-28; Ahlquist D A, et al., JAMA 1993; 269:1262-1267; Ahlquist D A, et al., N Engl J Med 1985; 312:1422-1428; Ahlquist D A, et al., Ann Intern Med 1984; 101:297-302; Schwartz S, et al., Clin Chem 1983; 29:2061-2067; Schwartz S, et al., Gastroenterology 1985; 89:19-26; each herein incorporated by reference in their entireties). Buffer (0.5 mol/L Tris, 10 mmol/L NaCl, 150 mmol/L EDTA, pH 9.0) (see, e.g., Olson J, et al., Diagn Mol Pathol 2005; 14:183-191; herein incorporated by reference in its entirety) preserved frozen stool slurry equivalent to 8 mg stool was used to perform HemoQuant test with an automated system in a clinical lab. Non-fluorescing heme in stool sample was converted to fluorescing porphyrins by removal of iron with 2 mL hot (60° C.) oxalic acid and 0.2 mL ferrous sulfate. The reaction mixture was then extracted with 3 mL ethyl acetate: isobutyl alcohol (11.1:1, v/v) followed by washing with 3 mL alkalinized aqueous solution of potassium acetate, and further extracted with 2.5 mL acetic acid/phosphoric acid. The extracted porphyrins, mostly protoporphyrin, are quantified based on fluorescence emission intensity at 652 nm using 405 nm as the excitation wavelength in an Infinite® 200 microplate reader (Tecan, Männedorf, Switzerland). Each plate consisted stool samples, standards, and negative and positive controls. Standards were made with known amounts of hemoglobin from human blood.

Statistical Analysis

Logistic procedure was used to calculate the correlation of stool long DNA and hemoglobin levels. Wilcoxon Rank Sum test was used to compare the long DNA or hemoglobin levels between each of the three different stool groups, and evaluate the association of marker levels with tumor location, gender, Dukes stage, and differentiation grade. The correlation of marker levels with tumor size and patient age was calculated with Logistic procedure. Chi-Square and Fisher exact tests were used to evaluate the association of detection rates of marker panel with clinical characteristics. Combination of long DNA and hemoglobin levels was calculated with a logistic model. Receiver Operating Curve (ROC) was constructed to compare long DNA and hemoglobin levels in cancers or adenomas versus normal subjects, and area under the curve (AUC) value was also calculated for each curve. Sensitivities were calculated at 90% specificity for single markers and their combination. Statistical analysis was conducted with SAS software (SAS Institute, Cary, N.C.).

Results

Figure 1B:
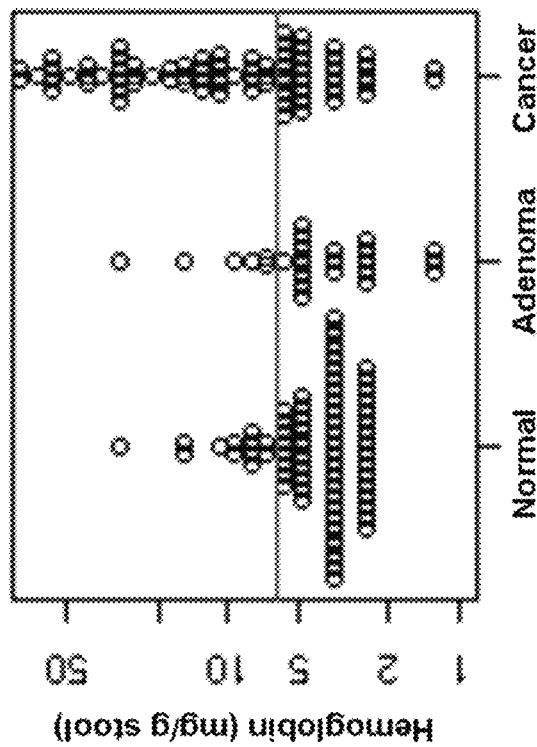
Figure 2:
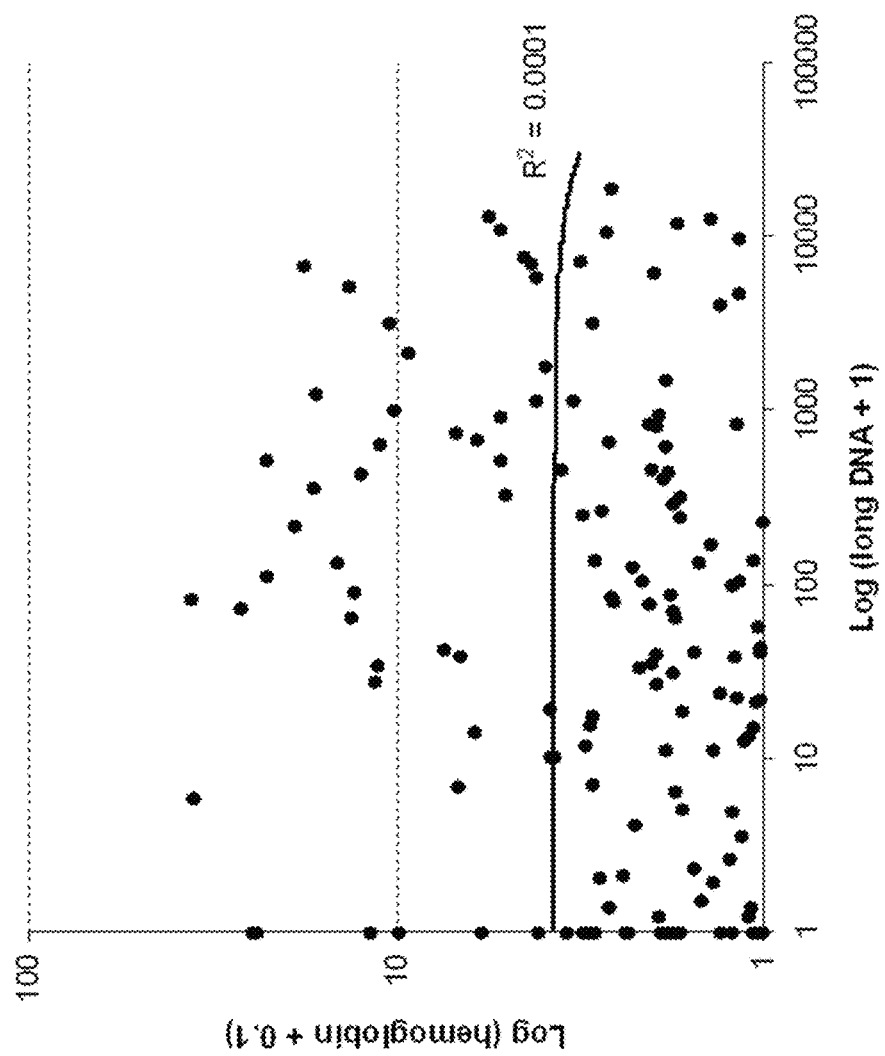
FIG. 2 shows correlation of long DNA with occult blood levels in stool samples displayed in a scatter plot graph. A black trend is drawn to show that fecal long DNA is not correlated with occult blood levels ($R^2=0.0001$). Because zero cannot be plotted in log scale, long DNA level plus 1 and occult blood level plus 0.1 are displayed here.

The median human DNA levels were 421 (range; 0-19140), 86 (0-6260), and 11 (0-30000) ng per g stools from patients with CRCs or adenomas, or from normal controls, respectively (p=0.0001, CRC vs normal; p=0.0005, adenoma vs. normal; p=0.007, CRC vs adenoma; FIG. 1A). The median hemoglobin levels were 3.4 (0.1-36.1), 1.5 (0.1-10.9), and 1.1 (0.3-11.0) mg per g stools from patients with CRCs or adenomas, or from normal controls, respectively (p=0.0001, CRC vs. normal or adenoma; p=1.0, adenoma vs normal; FIG. 1B). Fecal long DNA and occult blood levels were not correlated ($R^2$=0.0001; FIG. 2).

Figure 3B:
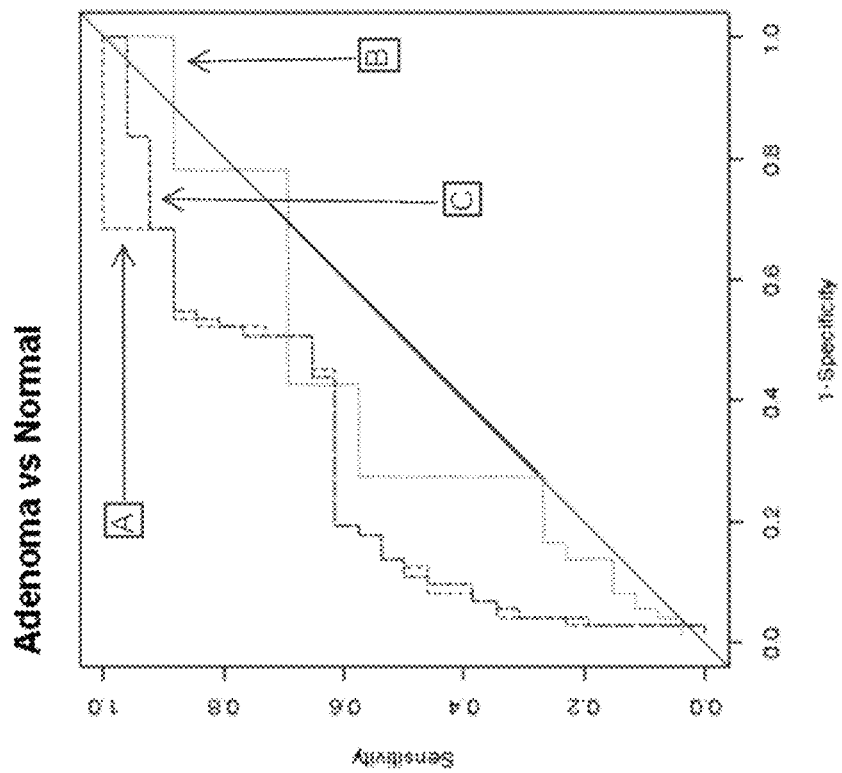
FIG. 3A-B shows receiver operating curves for stool long DNA and occult blood levels in patients with colorectal cancers or advanced adenomas versus normal controls. For cancers versus normal controls, AUC values were 0.82, 0.78, and 0.90 for fecal long DNA, occult blood, and combination testing, respectively; for advanced adenomas versus normal controls, AUC values were 0.72, 0.50, and 0.72 for fecal DNA, occult blood, and combination testing, respectively. A, B, and C represent receiver operating curves for fecal long DNA, occult blood, and combination testing, respectively.
Figure 3A:
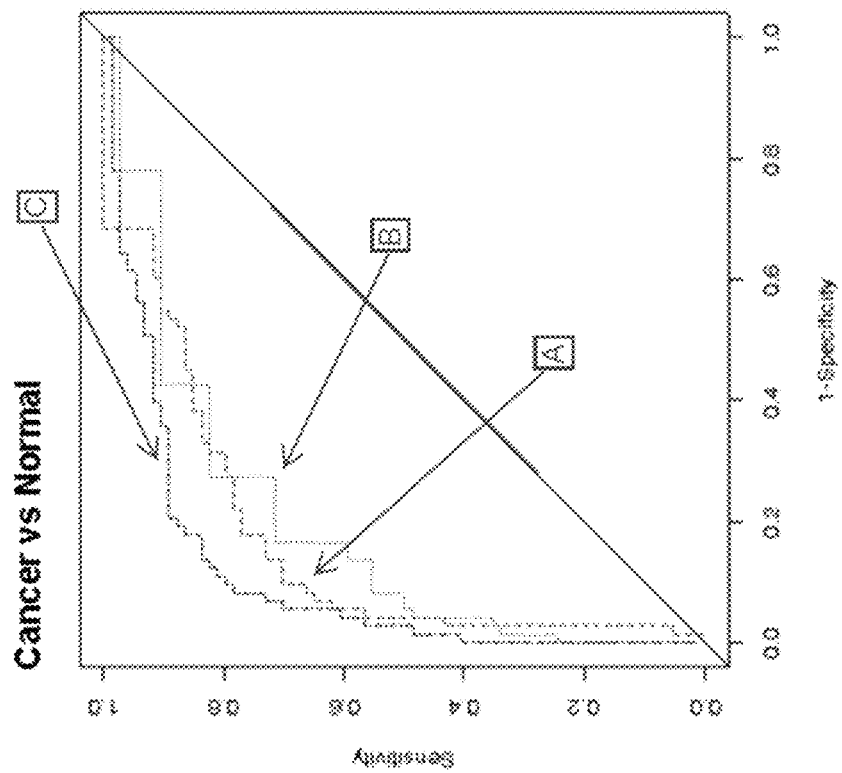

At 90% specificities, long DNA testing detected 70% of colorectal cancers and 46% of adenomas while occult blood testing detected 50% and 12% (FIGS. 1 & 3). Combining these tests detected 80% colorectal cancers and 46% of adenomas at 90% specificity (FIG. 3). For detection of colorectal cancer, AUC values were 0.82, 0.78, and 0.90 for fecal long DNA, occult blood, and combination testing, respectively (p=0.02, long DNA vs combination; p=0.0001, occult blood vs. combination; FIG. 3). For detection of advanced adenoma, AUC values were 0.72, 0.50, and 0.72 for fecal DNA, occult blood, and combination testing, respectively (p=0.8, long DNA vs combination; p=0.03, occult blood vs. combination; FIG. 3).

The median (range) fecal long DNA level was 181 (0-7120) ng/g stool with stage 1-2 cancers and 910 (0-19140) ng/g stool with stage 3-4 cancers, p=0.001; and 112 (0-4780) ng/g stool with proximal cancers and 1006 (0-19140) ng/g stool with distal cancers, p=0.0001. The median fecal occult blood level was 7.0 mg Hb/g (0.2-26.4 mg/g) with proximal cancers and 2.5 mg/g (0.1-36.1 mg/g) with distal ones, p=0.04. The median fecal long DNA and occult blood levels in stools from patients with CRCs and advanced adenomas were not associated with other clinical characteristics. Median size was 4.0 cm (1.0-15.0) for neoplasms detected by the combined tests and 3.7 cm (1.0-7.0) for neoplasms missed, p=0.02. Neoplasm detection rates by combined tests were affected by neither tumor site nor stage.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method comprising:
contacting a stool sample obtained from a human patient having or suspected of having colorectal cancer with a stool preservative buffer;
homogenizing the stool sample in contact with the stool preservative buffer;
amplifying of human DNA in the homogenized stool sample;
contacting human DNA amplified from the stool sample with one or more reagents that detect one or more exfoliated epithelial markers specific for a colorectal neoplasm;
detecting binding between one or more exfoliated epithelial markers specific for a colorectal neoplasm and the one or more reagents that detect one or more exfoliated epithelial markers specific for a colorectal neoplasm,
wherein the one or more exfoliated epithelial markers specific for a colorectal neoplasm comprise one or more colorectal neoplasm-specific nucleic acid markers selected from the group consisting of a gene having a point mutation, a gene reflecting microsatellite instability, and a gene having aberrant methylation,
wherein said gene having a point mutation is selected from the group consisting of K-ras, APC, melanoma antigen gene, p53, BRAF, BAT26 and PIK3CA,
wherein said gene reflecting microsatellite instability is BAT26,
wherein said gene having aberrant methylation is selected from the group consisting of bmp-3, bmp-4, SFRP2, vimentin, septin9, ALX4, EYA4, TFPI2, NDRG4, and FOXE1,
contacting the stool sample with one or more reagents that detect one or more fecal occult blood markers specific for a colorectal neoplasm;
detecting binding between the one or more fecal occult blood markers specific for a colorectal neoplasm and the one or more reagents that detect one or more fecal occult blood markers specific for a colorectal neoplasm,
wherein the one or more fecal occult blood markers specific for a colorectal neoplasm are selected from the group consisting of hemoglobin, alpha-defensin, calprotectin, α1-antitrypsin, albumin, MCM2, transferrin, lactoferrin, and lysozyme.

2. The method of claim 1, wherein the one or more fecal occult blood markers specific for a colorectal neoplasm is detected through a heme porphyrin test.

3. The method of claim 1, wherein the one or more fecal occult blood markers specific for a colorectal neoplasm is detected through a guaiac test.

4. The method of claim 1, wherein the one or more fecal occult blood markers specific for a colorectal neoplasm are detected through an immunochemical test.

5. The method of claim 1, wherein the preservative buffer comprises 0.5 mol/L Tris, 10 mmol/L NaCl, and 150 mmol/L EDTA, wherein the pH of the preservative buffer is pH 9.0.

* * * * *